United States Patent [19]

Roizman et al.

[11] Patent Number: 5,795,713
[45] Date of Patent: Aug. 18, 1998

[54] METHODS FOR IDENTIFYING INDUCERS AND INHIBITORS OF PROGRAMMED CELL DEATH

[75] Inventors: Bernard Roizman; Bin He, both of Chicago, Ill.

[73] Assignee: Arch Development Corporation, Chicago, Ill.

[21] Appl. No.: 795,470

[22] Filed: Feb. 4, 1997

Related U.S. Application Data

[60] Provisional application No. 60/036,997, Jan. 31, 1997.
[51] Int. Cl.$^6$ .............................. C12Q 1/42; C12Q 1/48; C12Q 1/70
[52] U.S. Cl. .................................. 435/5; 435/15; 435/21
[58] Field of Search .................................. 435/15, 21, 5

[56] References Cited

U.S. PATENT DOCUMENTS

5,632,994  5/1997  Reed et al. ........................... 424/198.1

FOREIGN PATENT DOCUMENTS

WO 93/19591  10/1993  WIPO.

OTHER PUBLICATIONS

He et al, Proc. Natl. Acad. Sci. USA, 94, 843–848, 1997.
Ackermann et al., "Identification by Antibody to a Synthetic Peptide of a Protein Specified by a Diploid Gene Located in the Terminal Repeats of the L Component of Herpes Simplex Virus Genome," *J. Virol.*, 58(3):843–850 (Jun. 1986).
Black et al., "Degradation of the Interferon–Induced 68,000–$M_r$ Protein Kinase by Poliovirus Requires RNA," *J. Virol.*, 67(2):791–800 (Feb., 1993).
Chou et al., "The Terminal a Sequence of the Herpes Simplex Virus Genome Contains the Promoter of a Gene Located in the Repeat Sequences of the L Component," *J. Virol.*, 57(2):629–637 (Feb., 1986).
Chou et al., "Herpes simplex virus 1 $\gamma_1 34.5$ gene function, which blocks the host response to infection, maps in the homologous domain of the genes expressed during growth arrest and DNA damage," *Proc. Nat'l Acad. Sci., USA*, 91:5247–5251 (Jun., 1994).
Chou et al., "Mapping of Herpes Simplex Virus–1 Neurovirulence to $\gamma_1 34.5$, a Gene Nonessential for Growth in Culture," *Science*, 250:1262–1266 (Nov. 30, 1990).
Chou et al., "The $\gamma_1 34.5$ gene of herpes simplex virus 1 precludes neuroblastoma cells from triggering total shutoff of protein synthesis characteristic of programmed cell death in neuronal cells," *Proc. Nat'l Acad. Sci., USA*, 89:3266–3270 (Apr., 1992).
Chou et al., "The Herpes Simplex Virus 1 Gene for ICP34.5, Which Maps in Inverted Repeats, Is Conserved in Several Limited–Passage Isolates but Not in Strain 17syn+," *J. Virol.*, 64(3) 1014–1020 (Mar., 1990).
Chou et al., "Differential Response of Human Cells to Deletions and Stop Codons in the $\gamma_1 34.5$ Gene of Herpes Simplex Virus," *J. Virol.*, 68(12):8304–8311 (Dec., 1994).

Chou et al., "Association of a $M_r$ 90,000 phosphoprotein with protein kinase PKR in cells exhibiting enhanced phosphorylation of translation initiation factor eIF–2α and premature shutoff of protein synthesis after infection with $\gamma_1 34.5$ mutants of herpes simplex virus 1," *Proc. Nat'l Acad. Sci., USA*, 92:10516–10520 (Nov., 1995).
Davies et al., "The E3L and K3L Vaccinia Virus Gene Products Stimulate Translation through Inhibition of the Double–Stranded RNA–Dependent Protein Kinase by Different Mechanisms," *J. Virol.*, 67(3):1688–1692 (Mar., 1993).
Ejercito et al., "Characterization of Herpes Simplex Virus Strains Differing in their Effects on Social Behavior of Infected Cells," *J. Gen. Virol.*, 2:357–364 (1968).
Fornace et al., "Mammalian Genes Coordinately Regulated by Growth Arrest Signals and DNA–Damaging Agents," *Mol. Cell. Biol.*, 9(10):4196–4203 (Oct., 1989).
Gross et al., "Identification of a $M_r$ =39,000 Phosphoprotein in Highly Purified Preparations of Rabbit Reticulocyte eIF–2 That Is Distinct from the $M_r$ =35,000 Subunit Phosphorylated by the Hemin–controlled Translational Repressor," *J. Biol. Chem.*, 255(13):6270–6275 (Jul. 10, 1980).
He et al., "The Carboxyl Terminus of the Murine MyD116 Gene Substitutes for the Corresponding Domain of the $\gamma_1 34.5$ Gene of Herpes Simplex Virus To Preclude the Premature Shutoff of Total Protein Synthesis in Infected Human Cells," *J. Virol.*, 70(1):84–90 (Jan., 1996).
Hershey, J.W.B., "Translational Control In Mammalian Cells, " *Annu. Rev. Biochem.*, 60:717–755 (1991).
Langland et al., "Products of the Porcine Group C Rotavirus NSP3 Gene Bind Specifically to Double–Stranded RNA and Inhibit Activation of the Interferon–Induced Protein Kinase PKR," *J. Virol.*, 68(6):3821–3829 (Jun., 1994).
Lee et al., "The 58,000–Dalton Cellular Inhibitor of the Interferon–Induced Double–Stranded RNA–Activated Protein Kinase (PKR) Is a Member of the Tetratricopeptide Repeat Family of Proteins," *Mol. Cell. Biol.*, 14(4):2331–2342 (Apr., 1994).
Lloyd et al., "Translational Stimulation by Reovirus Polypeptide σ3:Substitution for VAI RNA and Inhibition of Phosphorylation of the α Subunit of Eukaryotic Initiation Factor 2," *J. Virol.*, 66(12):6878–6884 (Dec., 1992).
Lord et al., "Sequence of MyD116 cDNA: a novel myeloid differentiation primary response gene induced by IL6," *Nucleic Acid Res.*, 18(9):2823 (1990).

(List continued on next page.)

*Primary Examiner*—David Saunders
*Attorney, Agent, or Firm*—Marshall, O'Toole, Gerstein, Murray & Borun

[57] ABSTRACT

Methods for identifying inducers and inhibitors of programmed cell death in a cell-free system are described. The methods exploit the finding that programmed cell death is accompanied by shutdown of cellular protein synthesis and by phosphorylation of eIF–2α and that the dephosphorylation of eIF–2α prevents the shutdown of protein synthesis.

16 Claims, 7 Drawing Sheets

OTHER PUBLICATIONS

Lu et al., "Binding of the Influenza NS1 Protein to Double-Stranded RNA Inhibits the Activation of the Protein Kinase That Phosphorylates the eIF-2 Translation Initiation Factor," *Virology*, 214:222–228 (1995).

McMillan et al., "HIV-1 Tat Directly Interacts with the Interferon-Induced, Double-Stranded RNA-Dependent Kinase, PKR," *Virology*, 213:413–424 (1995).

McNair et al., "Hepatitis delta replication in vitro is not affected by interferon-$\alpha$ or $-\gamma$ despite intact cellular responses to interferon and dsRNA," *J. Gen. Virol.*, 75:1371–1378 (1994).

Pathak et al., "Generation of a Mutant Form of Protein Synthesis Initiation Factor eIF-2 Lacking the Site of Phosphorylation by eIF-2 Kinases," *Mol. Cell. Biol.*, 8(2):993–995 (Feb., 1988).

Sharp et al., "Comparative analysis of the regulation of the interferon-inducible protein kinase PKR by Epstein-Barr virus RNAs EBER-1 and EBER-2 and adenovirus $VA_1$ RNA," *Nucleic Acid Res.*, 21(19):4483–4490 (1993).

Song et al., "Cloning and characterization of a human protein phosphatase 1-encoding cDNA," *Gene*, 129:291–295 (1993).

Swaminathan et al., "Simian Virus 40 Large-T Bypasses the Translational Block Imposed by the Phosphorylation of eIF-2$\alpha$," *J. Virol.*, 219(1):321–323 (May 1, 1996).

Autoradiogram

FIG. 3A

Immunoblot probed with anti-$\gamma_1$34.5 antibody

METHODS FOR IDENTIFYING INDUCERS AND INHIBITORS OF PROGRAMMED CELL DEATH

The U.S. government may own certain rights in the invention pursuant to grants from the National Cancer Institute (CA47451), from the National Institute for Allergy and Infectious Diseases (AI24009), and from the United States Public Health Service.

CROSS-REFERENCE TO RELATED APPLICATION

The 35 U.S.C. § 119(e) priority benefit of U.S. provisional patent application Ser. No. 60/036,997 filed Jan. 31, 1997, is claimed.

BACKGROUND OF THE INVENTION

Programmed cell death, or apoptosis is an active cellular mechanism and has several important implications. First, it is clear that such an active process can provide additional means for regulating cell numbers as well as the biological activities of cells. Secondly, mutations or cellular events which potentiate apoptosis may result in premature cell death. Third, a form of cell death that is dependent on a specific active cellular mechanism can at least potentially be suppressed. Finally, inhibition of programmed cell death may be expected to lead to aberrant cell survival and could be expected to contribute to oncogenesis, while conversely it is thought that tumor cell suicide may be induced through apoptosis or programmed cell death.

In general, programmed cell death involves distinctive morphological changes including nuclear condensation and degradation of DNA to oligonucleosomal fragments. In certain circumstances it is evident that apoptosis is triggered by or is preceded by changes in protein synthesis. For example, cellular protein synthesis may be significantly down-regulated. The DNA degradation described above may be a slow process, occurring days after the cessation of the cell's biosynthetic activities. Apoptosis appears to provide a very clean process for cellular destruction, in that the cells are disposed of by specific recognition and phagocytosis prior to bursting. In this manner cells can be removed from a tissue without causing damage to the surrounding cells. Thus, it can be seen that programmed cell death is important to a number of physiological processes, including morphological development, clonal selection in the immune system, and normal cell maturation and death in other tissue and organ systems.

It has also been demonstrated that cells can undergo apoptosis or programmed cell death in response to environmental stimuli. Examples include the appearance of a stimulus, such as glucocorticoid hormones for immature thymocytes, or the disappearance of a stimulus, such as interleukin-2 withdrawal from mature lymphocytes, or the removal of colony stimulating factors from hemopoietic precursors (for a review of literature see Williams, *Cell*, 65:1097–1098 [1991]). Furthermore, it has recently been demonstrated that the response to removal of nerve growth factor from established neuronal cell cultures that mimics target removal, or axiotomy, or other methods of trophic factor removal, is a triggering of a suicide program or programmed cell death. [See Johnson et al., *Neurobiol. of Aging*, 10:549–552 (1989)]. The authors proposed a "death cascade" or "death program," which envisions that trophic factor deprivation initiates the transcription of new mRNA and the subsequent translation of that mRNA into death associated proteins which act in sequence to ultimately produce "killer proteins." Such an intracellular mechanism seems to fit well with the characteristics of apoptosis discussed above, e.g., death of specific cells without the release of harmful materials and without the disruption of tissue integrity. Furthermore, the authors indicate that inhibitors of macromolecular synthesis prevented the death of neurons in the absence of nerve growth factor.

Studies have been conducted to explore the possibility that tumor cells could be eliminated by artificially triggering apoptosis. The anti-APO-1 monoclonal antibody induces apoptosis in several transformed human B and T cell lines. The antibody binds to a 52 kd surface protein and could act either by mimicking a positive death-inducing signal or by blocking the activity of a factor required for survival. Anti-FAS antibodies have similar effects. The recent cloning and sequencing of the gene for the FAS antigen has shown that it is a 63 kilodalton transmembrane receptor. Itoh et al., *Cell*, 66:233–243 (1991).

However, neither APO-1 nor FAS is likely to function exclusively as a trigger for cell death. Both are cell surface receptors that may activate quite different cellular responses under other circumstances. Moreover, these antigens are not confined to tumor cells and their effect on normal cells is certainly an important consideration, as is the possible appearance of variants that no longer display the antigens.

It has also been demonstrated that the cell death induced by a range of cytotoxic drugs, including several used in cancer therapy, has also been found to be a form of apoptosis [Barry et al, *Biochem. Biopharmacol.*, 40:2353–2362 (1990)]. This is also true, in many cases, for cell death after $\gamma$- or x-irradiation [Williams, *Cell*, 65:1097–1098 (1991)]. In fact, the failure of apoptosis or programmed cell death in tumor cells could be of fundamental importance in contributing not only to the evasion of physiological controls on cell numbers, but also to resistance both to natural defenses and to clinical therapy.

The expression of the bcl-2 gene has been shown to inhibit death by apoptosis. The bcl-2 gene was isolated from the breakpoint of the translocation between chromosomes 14 and 18 found in a high proportion of the most common human lymphomas, that being follicular B cell lymphomas. The translocation brings together the bcl-2 gene and immunoglobulin heavy chain locus, resulting in an aberrantly increased bcl-2 expression in B cells. Subsequently, Henderson et al., [*Cell*, 65:1107–1115 (1991)] demonstrated that expression of latent membrane protein 1 in cells infected by Epstein-Barr virus protected the infected B cells form programmed cell death by inducing expression of the bcl-2 gene. Sentman et al. [*Cell*, 67: 879–888 (1991)] demonstrated that expression of the bcl-2 gene can inhibit multiple forms of apoptosis but not negative selection in thymocytes. Strasser et al. [*Cell*, 67:889–899 (1991)] demonstrated that expression of a bcl-2 transgene inhibits T cell death and can perturb thymic self-censorship. Clem et al. [*Science*, 245:1388–1390 (1991)] identified a specific baculovirus gene product as being responsible for blocking apoptosis in insect cells. Gagliardini et al [*Science*, 263:826–828 (1994)] demonstrated the ability of the crmA gene product to prevent apoptosis in the dorsal root ganglion cells of chicken which had been deprived of nerve growth factor. More generally, Barinaga, [*Science*, 263:754–756 (1994)] also discusses the role of bcl-2, Bax(long), bclX(short) and ICE in apoptosis.

A number of diseases have been associated with apoptosis of neuronal cells. For example, amyotrophic lateral sclerosis (Lou Gehrig's disease) has been associated with apoptotic cell death. Alexianu et al., *J. Neurochem.* 63:2365–2368 (1994). Spinal muscular atrophy is associated with the partial deletion of an apoptosis inhibitory protein which results in apoptotic cell death, Roy et al., *Cell* 80:167–178 (1995). Huntington's disease has also been associated with apoptotic cell death. Portera-Cailliau et al., *J. Neurosci* 15:3775–3787 (1995). Apoptotic cell death has also been strongly implicated in Alzheimer's disease, Gschwind et al., *J. Neurochem* 65:292–300 (1995); and LaFerla et al., *Nat. Genet.* 9:21–30 (1995).

Thus it is clear that the ability to control apoptosis or programmed cell death, such as by inducing it to occur in cells (e.g. in tumor cells), or to prevent apoptosis or programmed cell death (e.g. in neurodegenerative conditions such as Alzheimer's disease, amyotrophic lateral sclerosis, Huntington's disease, spinal muscle atrophy, and other neurodegenerative disorders) will allow therapeutic intervention in diseases for which there are currently few if any therapeutic modalities. In order to achieve such therapeutic control, screening methods must be made available for identifying substances which induce or inhibit programmed cell death.

SUMMARY OF THE INVENTION

It is an object of the invention to provide methods for identifying inducers and inhibitors of programmed cell death in cell-free systems. More particularly, the invention is directed to methods for identifying inhibitors or inducers of programmed cell death or apoptosis which exert their effects by interacting with elements of the protein synthetic machinery of a cell when tested in a cell-free system.

The invention exploits the observation that cells whose protein synthesis is shut down as the result of certain stresses that provoke programmed cell death or apoptosis, exhibit increased ability to phosphorylate or to prevent dephosphorylation of eIF-2α. The invention also expolits the observation that proteins which have been shown to prevent programmed cell death such as $\gamma_1 34.5$ and GADD34 reduce the level of phosphorylation of eIF-2α.

According to the invention, an inhibitor of programmed cell death is identified by its ability to decrease the level of phosphorylation of phosphorylated eIF-2α or to prevent phosphorylation of eIF-2α in a cell-free system comprising PP1α and eIF-2α.

Inducers of programmed cell death are identified in a cell-free system of the invention by their ability to prevent the dephosphorylation of eIF-2α, to induce the phosphorylation of eIF-2α and/or to interact with (e.g. activate) PKR.

Other objects and advantages of the invention may be apparent to those skilled in the art from review of the following detailed description, taken in conjunction with the figures and the appended claims.

BRIEF DESCRIPTION OF THE FIGURES

FIGS. 5A through 5D illustrate phosphatase activity in S10 fractions of HeLa cells mock-infected, and of such cells infected with 20 pFU of HSV-1(F), R3616, or R8300 per cell.

DETAILED DESCRIPTION

Herpes simplex viruses have particular characteristics that make them useful for the study of programmed cell death (see, WO 93/19591 published 14 Oct. 1993 and references cited below, all of which are incorporated herein by reference). Herpes simplex virus 1 (HSV-1) encodes a gene, $\gamma_1 34.5$, whose function is to preclude a host response which terminates all protein synthesis subsequent to the onset of viral DNA synthesis [Chou et al., *Proc. Natl. Acad. Sci. USA* 89:3266–3270 (1992)]. The $\gamma_1 34.5$ gene maps in the sequences flanking the long unique sequence of HSV-1 DNA and therefore is present in two copies per genome [Chou et al., *J. Virol.* 57:629–637 (1986)]. The 263 amino acid protein encoded by the HSV-1(F) $\gamma_1 34.5$ consists of three domains, an amino terminal domain of 160 amino acid-domain, ten repeats of three amino acids (AlaThePro), and a 73 amino acid-carboxyl terminal domain [Chou et al., *J. Virol.* 64:1014–1020 (1990)]. A stretch of 64 amino acids at the carboxyl terminus of the $\gamma_1 34.5$ is homologous to a corresponding stretch of amino acids of the carboxyl terminus of a murine protein known as MyD116 and a Chinese hamster protein known as GADD34 [Chou et al., *Proc. Natl. Acad. Sci. USA* 89:3266–3270 (1992); McGeoch et al., *Nature (London)* 353:609 (1991)]. MyD116 is a member of a set of proteins induced in myelogenous leukemia cells induced for terminal differentiation by interleukin 6 [Lord et al., *Nucleic Acids Res.* 18:2823 (1990)]. GADD34, structurally closely related to MyD116, is also one of a subset of proteins induced following DNA damage or cell growth arrest [Fornace et al., *Mol. Cell. Biol.* 9:4196–4203 (1989); Fornace et al., *Ann. N.Y. Acad. Sci.* 663:139–153 (1992); Zhan et al., *Mol. Cell. Biol.* 14:2361–2371 (1994)].

Infection of human cells with herpes simplex virus in which both copies of $\gamma_1 34.5$ are inactivated or deleted, but particularly of human neuroblastoma cell line SK-N-SH or primary human foreskin fibroblasts results in nearly complete cessation of the host cell protein synthesis and the replicative cycle of the virus [Chou et al., *J. Virol.* 66:8304–8311 (1994)]. This total premature shutoff of protein synthesis is not seen in these cells when they are treated with inhibitors of viral DNA synthesis or in Vero cells [Chou et al., *Proc. Natl. Acad. Sci. USA* 89:3266–3270 (1992)].

The capacity to preclude total premature shutoff of protein synthesis maps in the carboxyl terminus domain of $\gamma_1 34.5$ protein that is homologous to the MyD116 protein [Chou et al., *Proc. Natl. Acad. Sci. USA* 91:5247–5251 (1994)]. Indeed, the carboxyl terminus of MyD116 successfully substitutes for the corresponding domain of $\gamma_1 34.5$. The viruses lacking the $\gamma_1 34.5$ protein or unable to express the carboxyl terminus of protein are totally avirulent in a murine encephalitis model of HSV-1 infections [Chou et al., *Science* 250:1262–1266 (1990); Whitley et al., *J. Clin. Invest.* 91:2837–2843 (1993); McKie et al., *J. Gen. Virol.* 75:733–741 (1994)].

Chou et al., *Proc. Natl. Acad. Sci. USA* 92:10516–10520 (1995) extended these observations and demonstrated that in wild-type or mutant infected cells, the double strand RNA-dependent protein kinase (PKR) was activated. However, only in cells infected with the $_{\gamma_1}$34.5-mutants lacking the $_{\gamma_1}$34.5 domain encoding the carboxyl terminus of the protein was the α subunit of eIF-2α phosphorylated.

The premature shut off of protein synthesis associated with programmed cell death raises several interesting questions, i.e. what triggers the host response, what is the mechanism by which protein synthesis is turned off, and what is the mechanism by which $_{\gamma_1}$34.5 precludes the host response.

The data set out below shows that (i) the carboxy terminus of MyD116 interacts with protein phosphatase 1α in yeast, and both MyD116 and $_{\gamma_1}$34.5 interact with protein phosphatase 1α in vitro; (ii) protein synthesis in infected cells is strongly inhibited by okadaic acid, a phosphatase 1 inhibitor; and (iii) the α subunit in purified eIF-2 phosphorylated in vitro is specifically dephosphorylated by S10 fractions of wild-type infected cells at a rate 3000 times that of mock-infected cells, whereas the eIF-2α-P phosphatase activity of $_{\gamma_1}$34.5⁻ virus infected cells is lower than that of mock-infected cells. The eIF-2α-P phosphatase activities are sensitive to protein phosphatase Inhibitor 2. In contrast to eIF-2α-P phosphatase activity, extracts of mock-infected cells exhibit a 2-fold higher phosphatase activity on [$^{32}$P] phosphorylase than extracts of infected cells. These results indicate that in infected cells, $_{\gamma_1}$34.5 interacts with and redirects phosphatase to dephosphorylate eIF-2α to enable continued protein synthesis despite the presence of activated PKR. The GADD34 protein may have a similar function in eukaryotic cells. The mechanism for maintenance of protein synthesis in the face of double-stranded RNA accumulation is different from that described for viruses examined to date.

Placing the foregoing observations into a broader context, in cells infected with HSV-1 accumulation of symmetric transcripts after the onset of DNA synthesis results in activation of PKR. A viral protein, $_{\gamma_1}$34.5 binds PP1α presumably through its carboxy terminus, and redirects the activity of the enzyme to dephosphorylate eIF-2α either by itself or in conjunction with other proteins. As a consequence, although PKR is activated, protein synthesis continues unabated. The following data support this scenario.

In cells infected with both wild-type and $_{\gamma_1}$34.5⁻ mutants, PKR is phosphorylated but only in cells infected with mutants lacking all or the 3' domain of the $_{\gamma_1}$34.5 gene is protein synthesis shut off and eIF-2α phosphorylated. The $_{\gamma_1}$34.5 sequence required to block protein synthesis shut off maps in the 3' domain of the gene and can be replaced without loss of function by the corresponding domain of MyD116, the murine GADD34 gene.

The eIF-2α-P phosphatase activities reported here may account for the differences in steady-state eIF-2α-P and protein synthesis previously noted in $_{\gamma_1}$34.5⁻ virus-infected cells [Chou et al., *Proc. Natl. Acad. Sci. USA* 92:10516–10520 (1995)]. Because PKR is not activated in mock-infected cells, the observed moderate eIF-2α-P phosphatase activity should be sufficient to prevent the degree of phosphorylation of eIF-2α required to inhibit protein synthesis. Wild-type HSV-1 infection does result in activation of PKR [Chou et al., *Proc. Natl. Acad. Sci. USA* 92:10516–10520 (1995)], but its effect is probably more than countered by the ~3000-fold increase in eIF-2α-P phosphatase. This marked increase in eIF-2α-P phosphatase activity is due to the expression of the $_{\gamma_1}$34.5 gene product, because infection with the $_{\gamma_1}$34.5⁻ mutant is associated with a decrease in eIF-2α-P phosphatase activity, that, upon activation of PKR, results in phsophorylation of eIF-2α and inhibition of protein synthesis [Chou et al., *Proc. Natl. Acad. Sci. USA* 92:10516–10520 (1995)].

In the yeast two-hybrid system the carboxyl terminus of MyD116 interacted with the human PP1α. The interaction of PP1α and MyD116 or with $_{\gamma_1}$34.5 protein was also demonstrable in pulldown experiments in vitro. The hypothesis that the eIF-2α phosphatase activity measured in cytoplasmic fractions of mock-infected or infected cells is derived from PP1 is strengthened by the observation that it was sensitive to inhibitor 2. Nevertheless, two lines of evidence suggest that this activity may represent a modified form of PP1α redirected to eIF-2α. Specifically, the eIF-2α-P phosphatase activity was less sensitive to inhibitor 2 than that of mock-infected cells, and furthermore, the phosphorylase phosphatase activity, a known function of PP1, was more potent in uninfected cells than in infected cells.

This work also sheds light on the putative function of GADD34. As noted above, the carboxyl terminus of the murine GADD34 gene (MyD1 16) is homologous to and can substitute for the corresponding domain $_{\gamma_1}$34.5 [He et al, *J. Virol.*, 70:84–90 (1996)]. It has also been shown that PP1α interacted with both $_{\gamma_1}$34.5 and MyD116 chimeric proteins in vitro (see below). These results argue that at least one of the functions of the GADD34 gene is similar to that of the $_{\gamma_1}$34.5 gene, and that the $_{\gamma_1}$34.5 gene may be useful in replacing its mammalian cell homolog to sustain protein synthesis in the face of stress that would naturally abolish protein synthesis by phosphorylation of eIF-2α.

Lastly, most viruses studied to date block phosphorylation of eIF-2α by encoding proteins which bind double stranded RNA, e.g., E2L of vaccinia [Davies et al., *J. Virol.* 67:1688–1692 (1993); Carroll et al., *J. Biol. Chem.* 268:12837–12842 (1993); and Yuwen et al., *Virology* 195:732–744 (1993)], α3 protein of Reo and rotaviruses [Langland et al., *J. Virol.* 68:3821–3829 (1994); Beattie et al., *J. Virol.* 69:499–505 (1995); Imani et al., *Proc. Natl. Acad. Sci. USA* 85:7887–7891 (1988); and Lloyd et al., *J. Virol.* 66:6878–6884 (1992)], and NS1 protein of influenza [Lu et al., *Virology* 214:222–228 (1995)], or proteins or RNA that inactivate PKR by binding to it, e.g., vaccinia K3L, Epstein-Barr virus EBERS1 and 2 [Sharp et al., *Nucleic Acids Res.* 21:4483–4490 (1993)], adenovirus VA1 RNA [Sharp et al., *Nucleic Acids Res.* 21:4483–4490 (1993); and Ghade et al., *J. Virol.* 68:4137–4151 (1994)], influenza virus-induced cellular p58 protein [Lee et al., *Mol. Cell. Biol.* 14:2331–2342 (1994)] or degrade PKR (poliovirus) [Black et al., *J. Virol.* 67:71–800 (1993)]. HIV-1 TAR sequence appears to bind to a cellular TAR binding protein and PKR [McMillan et al., *Virology* 213:413–424 (1995); Park et al., *Proc. Natl. Acad. Sci. USA* 91:4713–4717 (1994); and Consentino et al., *Proc. Natl. Acad. Sci. USA* 92:9445–9449 (1995)]. The exceptions may be hepatitis delta virus that does not activate PKR even though in vitro it consists largely of double-stranded RNA [McNair et al., *J. Gen. Virol.* 75:1371–1378 (1994)], and simian virus 40 whose large T antigen acts at a step postactivation of PKR [Swaminahan et al., *J. Virol.* 219:321–323 (1996)]. These data suggest that HSV-1 and HSV-2 use a very different mechanism to preclude the shutoff of protein synthesis by targeting phosphorylated eIF-2α rather than either PKR or double-stranded RNA.

The elucidation of these mechanisms provides the ability to develop new cell-free methods which are useful for the screening of both inducers and inhibitors of programmed cell death, such inhibitors or inducers of programmed cell death may provide useful therapeutic agents for the prevention of diseases associated with the induction of programmed cell death as well as therapeutics for diseases such as any of a wide variety of tumorigenic diseases in which it would be desirable to induce programmed cell death. Such systems are also useful for identifying antiviral substances which influence programmed cell death in infected cells by mechanisms discussed herein and as exemplified below. The following examples exemplify the practice of the invention and are not intended to limit the scope of the invention as recited in the claims.

Example 1 describes the cells and viruses used in the studies.

Example 2 demonstrates that the phosphorylation of eIF-2α is associated with a kinase present in a fraction enriched for ribosomes of cells infected with R3616 ($_{\gamma 1}$34.5$^-$) and in which protein synthesis was shut off. These data also show that immunoprecipitation of PKR from the same fraction after reaction with $|_\gamma{}^{32}P|$-ATP yielded several phosphorylated polypeptides.

Example 3 describes the cloning and expression of human protein phosphatase 1α.

Example 4 describes the measurement of eIF-2α phosphatase activity.

Example 5 describes the determination of phosphorylase and phosphatase activity.

Example 6 describes the interaction of GADD3y (MyD116) with PP1α in a yeast two-hybrid system, and the identification of PP1α.

Example 7 describes the binding of MyD116 and $_{\gamma 1}$34.5 to PP1α in vitro.

Example 8 describes the role of phosphatase activity in protein synthesis in infected cells.

Example 9 describes the activity of eIF-2 α phosphatase in wild type or R8300 recombinant virus infected cells.

Example 10 describes the sensitivity of eIF-2α phosphatase activity to PPα Inhibitor 2.

Example 11 demonstrates that activated phosphatase activity is specific for eIF-2α.

Example 12 describes methods for identifying inducers and inhibitors of programmed cell death in cell-free systems.

EXAMPLE 1

Cells and Viruses

Vero, HeLa cells, and the human neuroblastoma cells (SK-N-SH) from American Type Culture Collection, 12301 Parklawn Drive, Rockville, Md. 20852 were propagated in Dulbecco's modified Eagle's medium supplemented with 5% (Vero and HeLa cells) and 10% (SK-N-SH cells) fetal bovine serum, respectively. HSV-1(F) is the prototype HSV-1 strain used in these studies (Ejercito et al., *J. Gen. Virol.* 2:357–364 (1968)). The HSV-1 recombinant R3616 has been previously described [Chou et al., *Proc. Natl Acad. Sci. USA* 89:3266–3270 (1992); Chou et al., *Proc. Natl. Acad. Sci. USA* 91:5247–5251 (1994); and Chou et al., *Science* 250:1262–1266 (1990)]. R3616 virus lacks 1 Kb from the coding domains of both copies of $_{\gamma 1}$34.5 genes. In recombinant virus R8300, the sequence encoding the carboxyl terminal domain of the $_{\gamma 1}$34.5 gene was replaced with the corresponding domain of the MyD116 gene as described in He et al., *J. Virol.* 70:84–90 (1996).

EXAMPLE 2

An eIF-2α Kinase Activity is Associated with the Ribosomal Fraction in Cells infected with $_{\gamma 1}$34.5$^-$ Virus In view of the results described in Chou et al., *Proc. Natl. Acad. Sci. USA* 92:10516–10520 (1995), a series of studies was conducted to determine whether the premature shutoff of protein synthesis in human neuroblastoma cells infected with R3616 is due to modification (phosphorylation) of α subunit of the translation initiation factor eIF-2 via eIF-2α kinase activity. The experiments utilized HeLa cells inasmuch as eIF-2 appears to be more stable in lysates of this cell line. HeLa cells, like most human cell lines studied to date, are also affected by premature shutoff of protein synthesis in cells infected with $_{\gamma 1}$34.5$^-$ viruses.

Figure 1A:
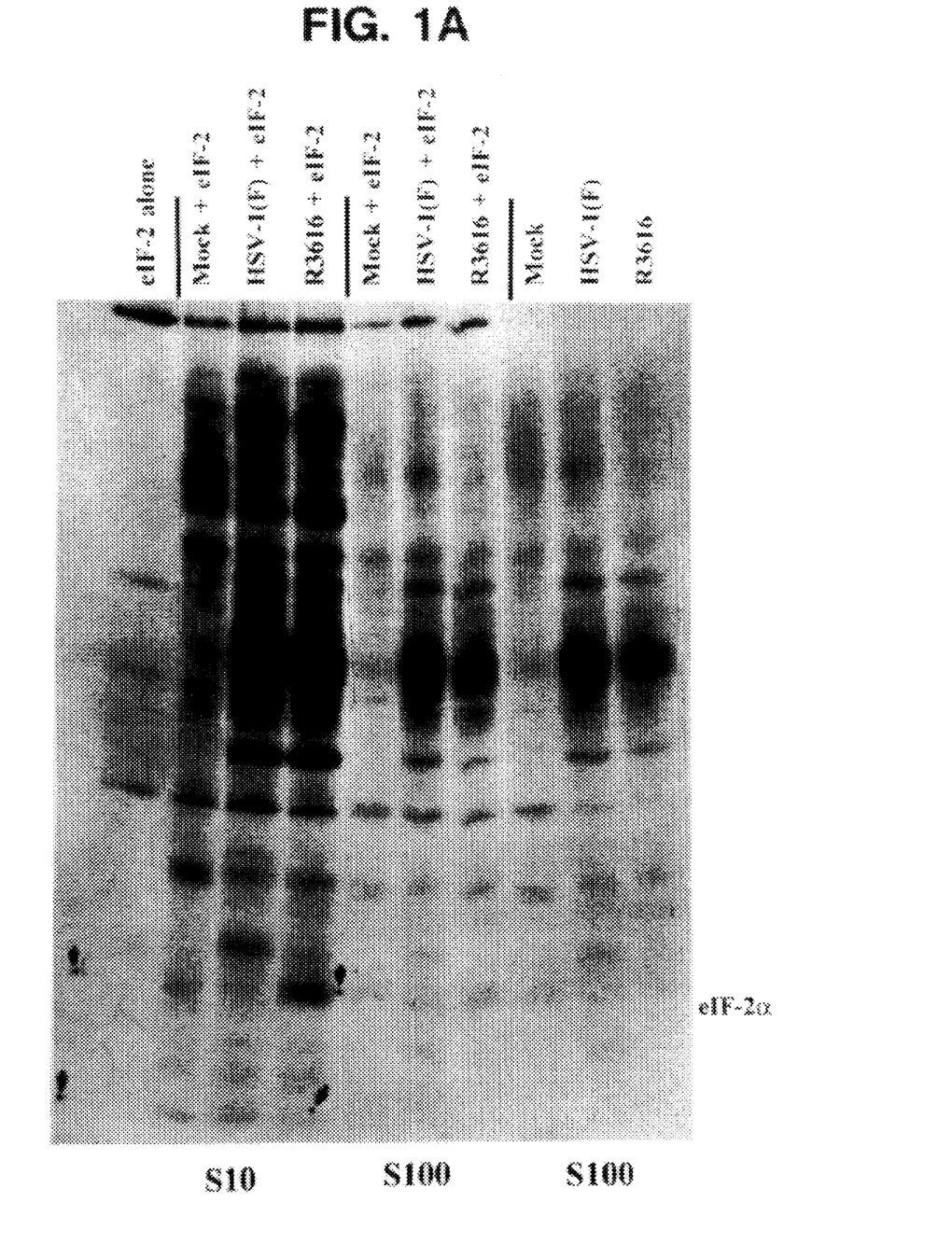
FIGS. 1A and 1B illustrate eIF-2α kinase activity in infected cells and mock infected cell extracts.
Figure 1B:
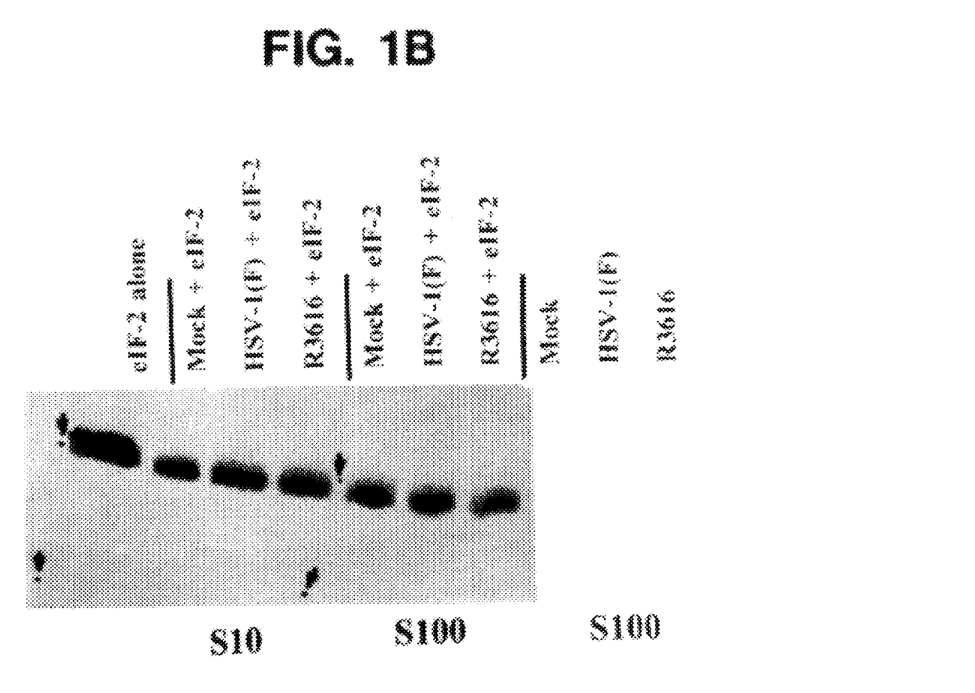

Replicate cultures of HeLa cells were either mock infected or infected with HSV-1(F) or R3616 viruses as described in Chou et al., *Proc. Natl. Acad. Sci. USA* 92:10516–10520 (1995). At seven hrs after infection the cells were harvested and S10 fractions, which includes all cytoplasmic materials (excluding mitochondria) were prepared according to procedures described by Pollard and Clemens (Pollard et al., *In Methods in Molecular Biology: New Nucleic Acid Techniques* (Walker, J. M., ed.), Chapter 5, pp.47–60, Humana Press, Clifton, N.J. (1988)). S100 fractions (post ribosomal) were supernatant fluids prepared from S10 fractions after centrifugation at 29,000 rpm for three hrs at 4° C. in a Beckman SW41 rotor. This fraction contained most of the soluble proteins but was free of ribosomes. Rabbit eIF-2 was purified from rabbit reticulocyte lysate according to the method describe by Grass et al., *J. Biol. Chem.*, 255:6270–6275 (1980) was used to detect the eIF-2α kinase activity present in those extracts. 0.2 µg of eIF-2 was reacted with the S10 or S100 fractions in the presence of $|_\gamma{}^{32}P|$-ATP (100 µCi per sample, Sp. act. 6000 Ci/mmol., NEN, Boston, Mass.) at 30° C. for 20 minutes. The reaction mixtures were then solubilized, electrophoretically separated on a denaturing 12% polyacrylamide gel crosslinked with N'N'-diallyltartardiamide, transferred unto nitrocellulose sheets and set for autoradiography as previously described (Chou et al., *Proc. Natl. Acad. Sci. USA* 89:3266–3270 (1992)). FIG. 1 shows the results of the analysis. Lanes with exogenous eIF-2 added were indicated on the extreme left. The position of eIF-2α is shown on the right.

As shown in FIG. 1, Panel A, eIF-2α subunit was extensively phosphorylated in the S10 extracts of R3616 infected cells, minimally phosphorylated in wild type- or mock-infected cells, and not phosphorylated at all in the absence of cell extracts. These results indicate that the S10 fraction of the $_{\gamma 1}$34.5$^-$ virus-infected cells contained an eIF-2α kinase activity that was much reduced or absent in similar extracts of mock-infected or wild type-infected cells. This activity was absent from all S100 fractions tested suggesting that the kinase activity is associated with ribosomes. In the absence of exogenous eIF-2, minimal phosphorylation of endogenous eIF-2 was observed in all extracts due to steady state phosphorylation and de-phosphorylation processes in the cell.

FIG. 1, Panel B shows a photograph of a nitrocellulose sheet containing separated proteins stained with monoclonal antibody specific to eIF-2α (Scorsone et al., *J. Biol. Chem.* 262:14538–14543 (1987)). After reacting with appropriate secondary antibody, the blot was developed with color reagents provided by Promega (Madison, Wis.) to identify the eIF-2α polypeptide. Arrows indicate the dots used to orient and align the phosphorylated eIF-2α polypeptide in panel A with the antibody stained eIF-2α polypeptide in Panel B. The data in panel B of FIG. 1 show that the level of eIF-2α was similar in all samples to which it had been added.

This activity was not present in mock-infected or wild type-infected cells. eIF-2 binds Met-tRNA$^f$ and GTP in a ternary complex which then associates with ribosomal subunits in a pre-initiation complex (Merrick, W. C., *Microbiological Reviews* 56:291–315 (1992); Hershey, J. W. B., *Annu. Rev. Biochem.* 60:717–755 (1991)). After initiation, eIF-2 is recycled off the 80S complex with the help of eIF-2B, another translational factor. One of the events that regulates translation is the phosphorylation of the α subunit of the eIF-2 complex. Phosphorylation of eIF-2α correlates with shut off of protein synthesis in heme-regulated hemopoietic cells, in response to growth inhibition, cellular stresses caused by virus infections, heat shock, heavy metals, deprivation of serum, amino acids, or glucose (Hershey, J. W. B., *Annu. Rev. Biochem.* 60:717–755 (1991); Sarre, T., *BioSystems* 22:311–325 (1989)). These effects have been linked to the phosphorylation of the $ser_{51}$ of eIF-2α either by PKR, a $M_r$ 68,000 a kinase also know as dsI, a double stranded RNA activated eIF-2α kinase which autophosphorylates itself, or by HRI, a heme regulated eIF-2α kinase (Merrick, W. C., *Microbiological Reviews* 56:291–315 (1992); Hershey, J. W. B., *Annu. Rev. Biochem.* 60:717–755 (1991)). A primary role of the phosphorylation of $ser_{51}$ in the regulation of protein synthesis is supported by the observation that substitution of the $ser_{51}$ with Ala precludes phosphorylation and maintains protein synthesis (Pathak et al., *Mol Cell Biol.* 8:993–995 (1988)).

EXAMPLE 3

Cloning and Expression of Human Protein Phosphatase α (PP1α)

The plasmid pRB4891, containing a 1.37 Kb cDNA encoding human protein phosphatase 1α(PP1α) was isolated from a commercially available human brain cDNA library (Stratagene). To construct pRB4890, a BamHI-EcoRI DNA fragment encoding codons 524 to 657 of MyD116 was amplified by PCR from a cDNA copy of the gene described by He et al., *J. Virol.* 70:84–90 (1996) with the primers TGACTGGATGCAGAGGCGGCTCAGATTGTTC (SEQ ID NO. 1) and AGCGCGCAATTAACCCTCACTAAAG (SEQ ID NO. 2) and inserted into the BamHI-EcoRI sites of pGBT9 (Clontech) to serve as "bait" in the two-hybrid system. The PCR conditions were 94° C. 2 min, 60° C. 3 min and 72° C. 3 min for 25 cycles. pRB4892 containing the chimeric GST-PP1α a gene was constructed by ligating a 0.9 Kb PCR fragment containing the entire coding sequence of PP1α except the first methionine codon into the EcoRI-SalI sites of pGEX4T-1 (Pharmacia). The oligonucleotide primers were GCACTGAATTCTCCGACAGCGAGAAGCTCAAC (SEQ ID NO. 3) and GCACTGTCGACATCTGGGGCACAGGGTGGTGT (SEQ ID NO. 4). To construct pRB4893 carrying a chimeric glutothione S transferase (GST)-carboxyl terminal domain of $_{γ1}$34.5 [GST-$_{γ1}$34.5(C)], the EcoRI-SalI fragment encoding codons 146 to 263 of $_{γ1}$34.5 from pRB71 and cloned into the EcoRI-SalI sites of pGEX4T-1. The construction of pRB4873 containing an AccI-EcoRI fragment encoding the 3' terminal 174 codons of MyD116 fused in frame to GST [GST-MyD116 (C)] was as reported by He et al., *J. Virol.* 70:84–90 (1996). Expression of GST-MyD116(c), GST-$_{γ1}$34.5(C) and GST-PP1 fusion proteins was induced by the addition of isopropyl-β-D-thiogalactoside to the medium with *Escherichia coli* BL21 cells transformed with either plasmid pRB4873, pRB4892 or pRB4892, followed by affinity purification of the fusion proteins from bacterial lysates on agarose beads conjugated with glutathione.

EXAMPLE 4

Determination of eIF-2α Phosphatase Activity

The translation initiation factor eIF-2 was purified from rabbit reticulocyte ribosomes according to a method of Gross et al., *J. Biol. Chem.* 255:6270–6275 (1980). A hemin-controlled translational repressor (HCR) was partially purified to step 4 from rabbit reticulocyte lysates according to the method described by Gross et al., *Biochem. Biophys. Res. Comm.* 50:832–838 (1983). eIF-2 (20 pmol or 2.7 μg) was reacted with step 4 HCR in 0.02M Tris-HCl, pH 7.5, 40 mM KCl, 2.0 mM $MgCl_2$, and 0.17 mM $|_γ{}^{32}P|$ ATP (2–10 Ci or 74–370 GBq/mmol) in a final volume of 12 μl for 25 min at 34° C. to yield phosphorylated eIF-2α and eIF-2β (1.0 and 0.7 mol/mol of eIF-2, respectively). HeLa cells were harvested 15 hrs after mock infection or infection with 20 PFU of HSV-1(f), R3616 or R8300 per cell. S10 fractions were prepared from lysates of mock-infected or infected cells as described by Chou et al., *Proc. Natl. Acad. Sci. USA* 92:10516–10520 (1995) and diluted to a final volume of 18 μl with 0.02M Tris-HCl, pH 7.5, 50 mM KCl, 2 mM $MgCl_2$, and 0.1 mM EDTA. ATP was then added to a final concentration of 0.8 mM. After 30 seconds at 34° C., each sample received 1.2 μl (2 pmol) of eIF-2($α^{32}P$) and was reincubated at 34° C. The rate of dephosphorylation of eIF-2($α^{32}P$) was determined by a method according to Gross et al., *Biochim. Biophys. ACTA* 740:255–263 (1983) by placing 6.0 μl aliquots into a solution containing SDS at times indicated in the figures, followed by electrophoresis on 7% denaturing polyacrylamide gels as described for 21 hrs at 44 V (3 V/cm), staining with Coomassie Blue, or Silver, drying, and autoradiography. $^{32}P$ remaining in eIF-2($α^{32}P$) was quantified by excising this band and comparing its Cerenkov radiation to that of equivalent aliquotes of eIF-2($α^{32}P$) that were not further incubated and were subjected to electrophoresis in parallel.

EXAMPLE 5

Determination of Phosphorylase and Phosphatase Activity

Phosphorylase b (32 μg, Sigma) was phosphorylated by incubation with 3.3 μg of phosphorylase kinase (Sigma, St. Louis, Mo.) in 0.01M Tris-HCl, pH7.5, 2.0 mM $MgCl_2$, and 0.13 mM $[_γ{}^{32}P]$ ATP (3 Ci or 111 GBq/mmol) in a final volume of 15 μl at 34° C. for 10 min. Dephosphorylation was determined by adding 4.4 μg of [$^{32}P$] phosphorylase to samples constituted and incubated as described in Example 4 in a final volume of 27 μl. At 1.5, three, six and ten min., 6.0 μl aliquotes were removed and processed as described above for determining phosphatase activity.

EXAMPLE 6

The Carboxyl Terminus of the Murine GADD34 Protein MyD116) Interacts with PP1α in the Yeast Two-Hybrid System The yeast strain Y190 (16) transformed with plasmid pRB4890, and growing on Trp- selective medium was retransformed with a human brain cDNA library (CLONTECH) and subjected to selection on Trp⁻/Leu⁻/His⁻ medium in the presence of 25 mM 3-aminotriazole (Sigma). Moderate to fast growing colonies five days after plating were restreaked on Trp⁻/Leu⁻/His⁻ medium. The library derived plasmids were recovered by transformation of *E. coli* HB101 with total yeast DNA preparations, followed by selection on Leu⁻/ampicillin⁺ medium as previously described in Durfee et al., *Gene Devel.* 7:555–569 (1993). The filter assay for β-galactosidase was done as recommended by Clontech.

As discussed briefly above, the two-hybrid system is particularly useful for cloning genes which encode proteins which interact with a protein of interest. See Fields et al., *Nature* 340:245–246 (1989) and Chien et al., *Proc. Natl. Acad. Sci. USA* 88:9578–9582. The carboxyl terminus of MyD116 was selected as bait for the two-hybrid system because (i) it and $_{\gamma_1}$34.5 share amino acid sequence homology [see Chou et al., *Proc. Natl. Acad. Sci. USA* 91:5247–5251 (1994) and McGeoch et al., *Nature* (London) 353:609 (1991)], (ii) the carboxyl terminus of MyD116 can substitute functionally for that of the $_{\gamma_1}$34.5 protein, and (iii) the codon usage of MyD116, a mammlian gene, is closer to that of yeast than that of HSV-1. Of the $10^6$ yeast colonies screened, only one colony was positive for β-galactosidase expression. The cDNA recovered from this colony was retransformed into yeast strain Y190 with various control plasmids encoding fusion proteins. These studies indicated that only the carboxyl terminus of MyD116 interacted with the protein encoded by the isolated cDNA. DNA sequence analysis revealed that the isolated cDNA encoded the catalytic subunit of protein phosphatase 1α (PP1α). See Song et al., *Gene* 129:291–295 (1993).

EXAMPLE 7

Both MyD116 and $_{\gamma_1}$34.5 Proteins Bind PP1α In Vitro

Figure 2A:
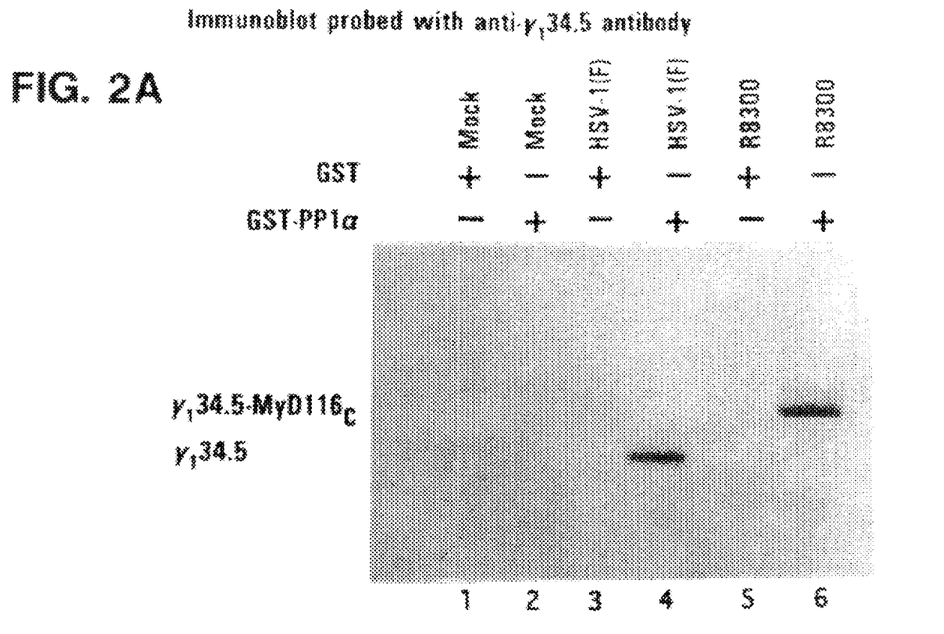
FIGS. 2A and 2B illustrate the association of phosphatase 1α with $\gamma_1 34.5$ and MyD116.

To verify and extend the observations that MyD116 and PP1α interact in yeast, a chimeric GST-PP1α gene constructed as described in Example 3 above was expressed in *E. coli*. Replicate HeLa cell cultures were harvested in lysis buffer containing 10 mM Hepes, pH 7.6, 250 mM NaCL, 10 mM MgCl$_2$, 1% Triton X-100, 0.5 mM PMSF and 2 mM benzamidine 18 hrs after mock-infection or infection with 10 PFU of HSV-1(F) or R8300 per cell. After 30 min on wet ice and low speed centrifugation to remove nuclei, the supernatant fluids were precleared with GST-beads and then reacted with GST-phosphatase 1 bound beads at 4° C. overnight. After extensive rinsing, the proteins bound to beads were solubilized by boiling in disruption buffer containing 50 mM Tris-HCl, pH7.0, 5% β-mercaptoethanol, 2% SDS, and 2.75% sucrose, electrophoretically separated on denaturing 12% polyacrylamide gels, transferred to a nitrocellulose sheet, and the blot was probed with anti-$_{\gamma_1}$34.5 serum directed to the Ala Thr Pro present in both $_{\gamma_1}$34.5 and the chimeric $_{\gamma_1}$34.5-MyD116 chimeric protein expressed by R8300. The position of $_{\gamma_1}$34.5 protein and of the chimeric protein $_{\gamma_1}$34.5-MyD116 are shown in FIG. 2A. As shown in FIG. 2A, the GST-PP1α protein bound both $_{\gamma_1}$34.5 from lysates of HSV-1(F) infected cells and the more slowly migrating $_{\gamma_1}$34.5-MyD116 chimeric protein from cells infected with R8300. GST alone did not react with either protein in the appropriate cell lysates.

In a second experiment, purified PP1α was mixed with beads carrying GST or chimeric proteins consisting of GST fused to the amino acids 146 to 263 of $_{\gamma_1}$34.5 or to amino acids 485 to 657 of MyD116 as follows.

An aliquot of GST-PP1α fusion protein bound to beads was reacted with 25 units of thrombin (Sigma, St. Louis Mo.) in PBS saline buffer at room temperature. After eight hrs, the mixture was spun in a table top centrifuge and the supernatant fluid containing PP1α was then dialyzed against lysis buffer, reacted with GST, GST-MyD116(C) or GST-$_{\gamma_1}$34.5(C) bound to beads and processed as described in Panel A. PP1 was detected with anti-phosphatase 1α antibody (Upstate Biotechnology Incorporated).

Figure 2B:
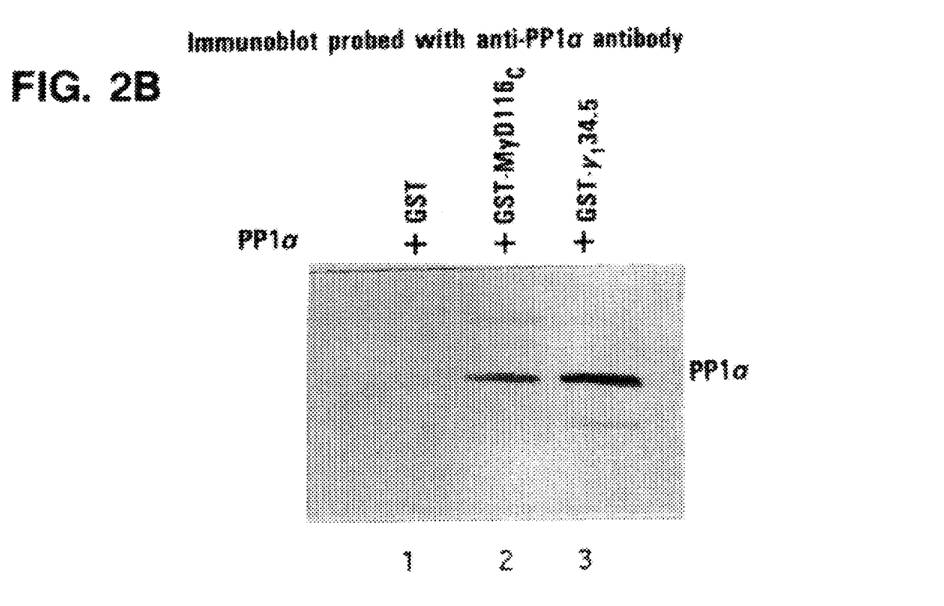

The proteins bound to GST or to the chimeric proteins were solubilized, subjected to electrophoresis on a denaturing gel, and reacted with anti-PP1α antibody. As shown in FIGS. 2A and 2B, both chimeric proteins but not GST brought down a protein with an apparent M$_r$ of 38,000 (molecular weight markers not shown) and which reacted with the anti-PP1α antibody.

EXAMPLE 8

Phosphatase Activity is Essential for Protein Synthesis in Infected Cells

Figure 3A:
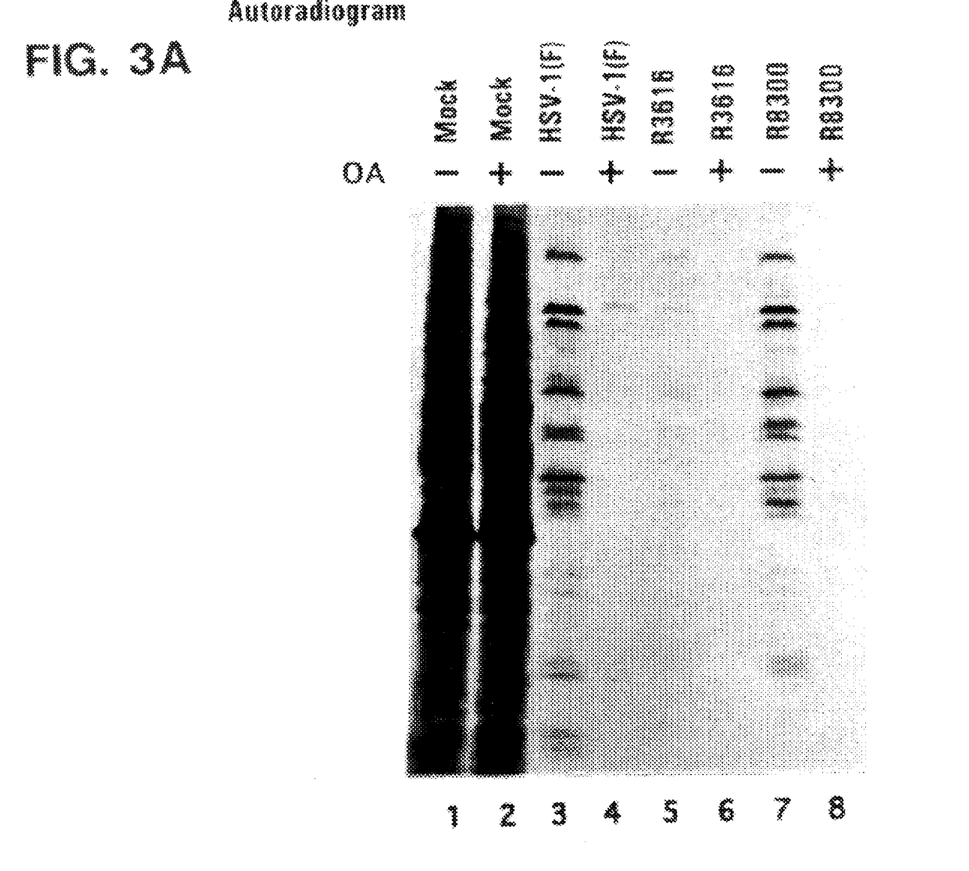
FIGS. 3A and 3B show autoradiographic images of electrophoretically separated $^{35}$S-methionine labelled proteins from cell lysates infected with the indicated viruses in the presence or absence of okadaic acid.

Tests were conducted to determine whether phosphatase activity is essential for sustained protein synthesis in infected cells. [$^{35}$S]methionine-labeled proteins from cell lysates were infected with the indicated viruses in the presence or absence of okadaic acid (OA). SK-N-SH cells were either mock infected or infected with 20 PFU of HSV-1(F), R3616, or R8300 per cell. At two hrs after exposure to the viruses, the cells were overlaid with medium 199V [Ackermann et al., *J. Virol.* 58:843–850 (1986)] supplemented with or without okadaic acid (25 ng/ml). At 14 hrs after infection, the cells were overlaid for one hr with one ml of medium 199V lacking methionine but supplemented with 50 µCi of [$^{35}$S]methionine (specific activity, >1000Ci/mmol; Amersham) for one hr, then harvested, solubilized in disruption buffer, subjected to electrophoresis in denaturing 12% polyacrylamide gels, transferred to a nitrocellulose sheet and subjected to autoradiography as described elsewhere [Chou et al., *Proc. Natl. Acad. Sci. USA*, 89:3266–3270 (1992)]. The results (FIG. 3A) show okadaic acid totally inhibited protein synthesis in cells infected with wild type HSV-1(F), the $_{\gamma_1}$34.5$^-$ virus R3616, or the R8300 recombinant expressing the $_{\gamma_1}$34.5-MyD116 chimeric protein. In contrast, okadaic acid had no apparent effect on protein synthesis in mock-infected cells.

Figure 3B:
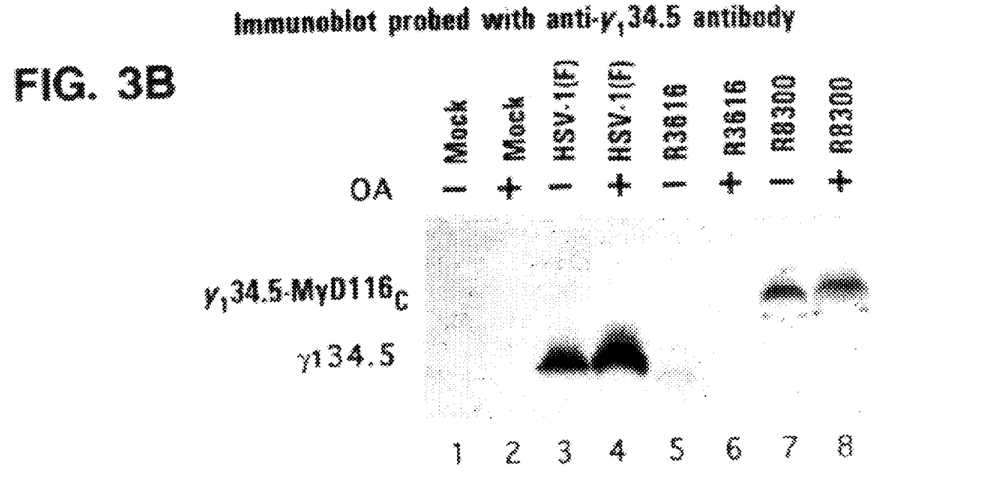

To test a trivial hypothesis that okadaic acid blocked in some fashion the synthesis of $_{\gamma_1}$34.5 or the $_{\gamma_1}$34.5-MyD116 proteins in infected cells, the lysates of cells infected with wild type and recombinant viruses were solubilized, subjected to electrophoresis in denaturing gels, electrically transferred to a nitrocellulose sheet and reacted with antibody to the $_{\gamma_1}$34.5 protein. As shown in FIG. 3B, the lysates of cells infected with HSV-1(F) or with R8300 expressed $_{\gamma_1}$34.5 or $_{\gamma_1}$34.5-MyD116 protein, respectively. The antibody did not react with lysates of mock-infected cells or cells infected with $_{\gamma_1}$34.5$^-$ virus.

EXAMPLE 9

Figure 4:
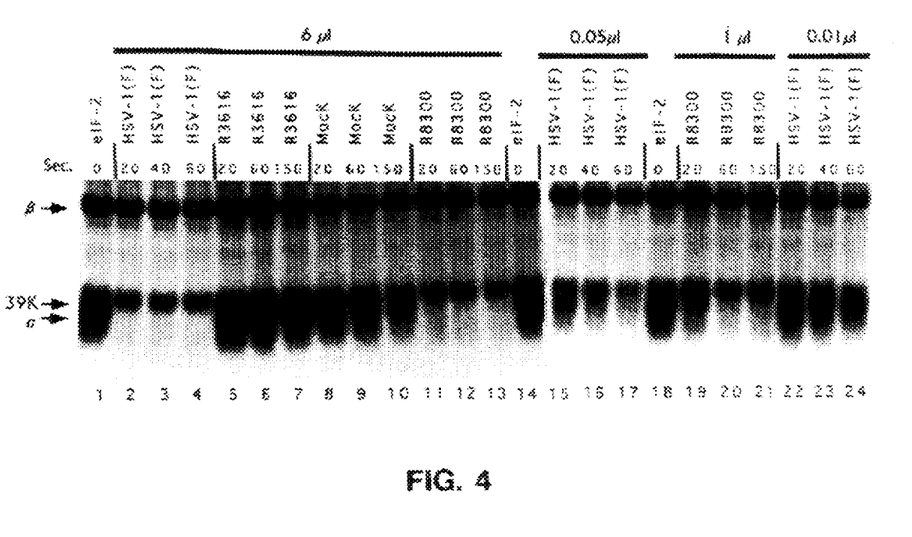
FIG. 4 depicts autoradiographic images of electrophoretically separated eIF-2 after reaction with variants of cells mock infected, and of cells infected with HSV-1(F), R3616, and R8300.

The eIF-2($\alpha^{32}$P) Phosphatase Activity is Highly Abundant in Wild-Type of T8300 Recombinant Virus-Infected Cells and Signigicantly Decreased In $_{\gamma_1}$34.5 Virus-Infected Cells Experiments were conducted to ascertain whether the shutoff of protein synthesis in cells infected with $_{\gamma_1}$34.5$^-$ virus R3616 was determined by the level of eIF-2α phosphatase activity. S10 fractions were prepared from lysates of HeLa cells either infected or mock-infected and tested for their ability to dephosphorylate eIF-2($\alpha^{32}$P). Unreacted eIF-2($\alpha^{32}$P) (FIG. 4, lanes 1, 14, 18) showed three labeled bands representing eIF-2α, eIF-2β(arrows), and a small amount of a M$_r$ 39,000 protein (arrow) that is a contaminant distinct from eIF-2α [See, Gross et al., *J. Biol. Chem.* 255:6270–6275 (1980)]. Reaction of this eIF-2 with the S10 fraction from mock-infected cells showed a moderate rate of loss of radioactivity from eIF2 ($\alpha^{32}$P) (FIG. 4 and FIGS. 5A–5D). This eIF-2($\alpha^{32}$P) phosphatase activity was reduced approximately three-fold in cells infected with $_{\gamma_1}34.5^-$ virus. In sharp contrast, the S10 fraction of cells infected with the wild type virus or with the R8300 mutant virus exhibited so marked a level of eIF-2($\alpha^{32}$P) phosphatase activity that virtually all added eIF-2($\alpha^{32}$P) radioactivity was removed within the first 20 seconds of reaction (FIG. 4, lanes 2 and 11). To verify that this phosphatase activity does not continue after the reaction mixture is mixed with the SDS denaturing solution, it was tested and found that eIF-2($\alpha^{32}$P) is completely stable following addition to a mixture of SDS and S10 fraction from cells infected with either wild type or R8300 recombinant virus.

To quantify the increase in eIF-2($\alpha^{32}$P) phosphatase activity associated with wild type or R8300 recombinant virus infection of HeLa cells, the S10 fractions from these cells were progressively diluted until the rate of dephosphorylation of eIF-2($\alpha^{32}$P) could be measured accurately. Only when the S10 fraction of wild type infected cells was diluted 600 fold could the eIF-2($\alpha^{32}$p) phosphatase activity be measured accurately, and it was still five fold greater than that of mock-infected cells (FIG. 4 and FIGS. 5A–5D). These findings indicate that the eIF-2($\alpha^{32}$P) phosphatase activity of wild type infected cells increased approximately 3000 fold. Similar analyses indicated that in cells infected with the R8300 recombinant virus this activity increased approximately 50 fold (FIGS. 4 and 5A–5D). The removal of radioactivity in these samples represented dephosphorylation and not proteolysis inasmuch as it was not associated with loss of eIF-2$\alpha$ protein is measured by staining. In addition, the marked increased in eIF-2($\alpha$P) phosphatase activity seen in S10 fractions of wild type virus-infected cells may be specific for eIF-2$\alpha$ inasmuch as neither the $M_r$ 39,000 phosphoprotein nor eIF-2($\beta^{32}$P) was significantly affected under the same conditions (FIG. 4). Finally, the results shown in FIGS. 4 and 5A–5D were reproducible and obtained in two determinations with each of three S10 fraction from mock-infected or infected HeLa cells.

EXAMPLE 10

The eIP-2($\alpha$P) Phosphatase Activity is Sensitive to PP1$\alpha$ Inhibitor 2

Figure 5A:
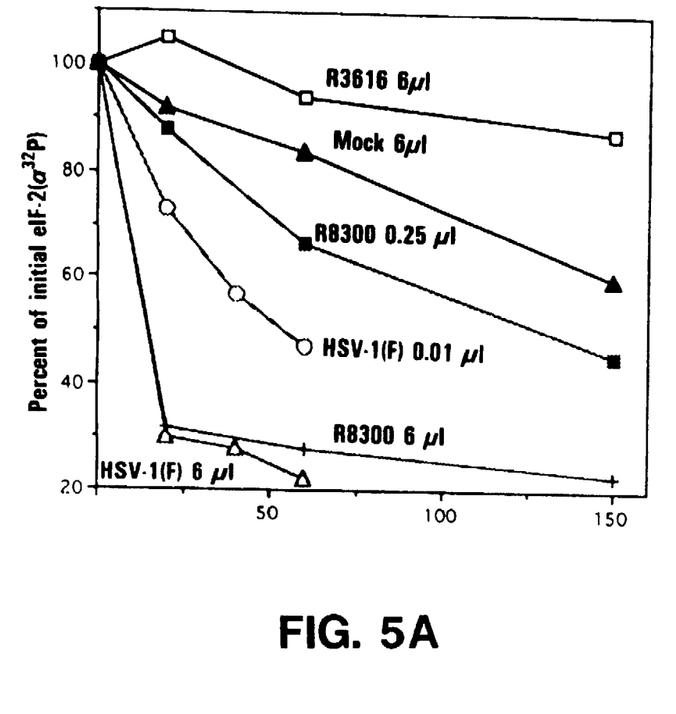
FIG. 5A shows residual radio-activity in eIF-2α after reaction with variable amounts of S10 fractions from mock-infected or infected cells.
Figure 5B:
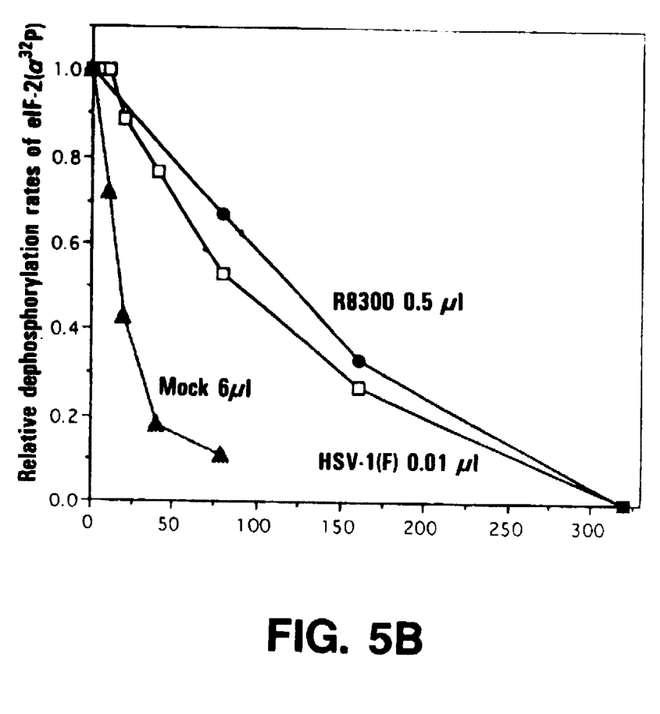
FIG. 5B shows the effect of inhibitor 2 on the rate of dephosphorylation of eIF-2α 1α$^{32}$P by the phosphatase activity in the S10 fractions.
Figure 5C:
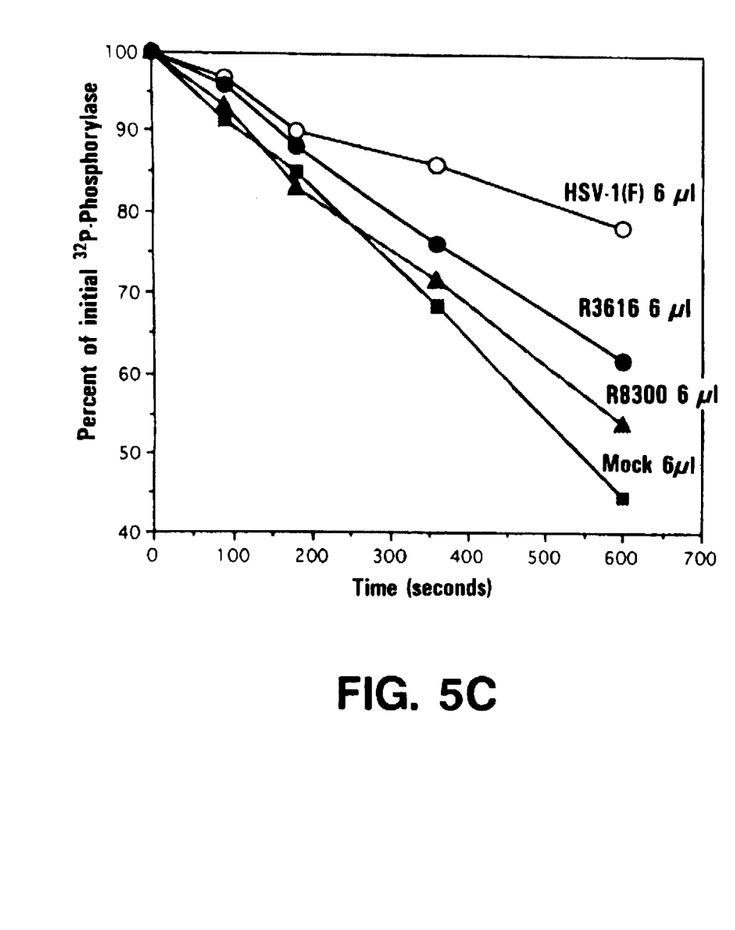
FIG. 5C shows $^{32}$P-phosphorylase phosphatase activity.

To determine whether eIF-2($\alpha^{32}$P) was dephosphorylated by PP1$\alpha$, the rate of dephosphorylation of eIF-2($\alpha^{32}$P) as a function of the concentration of Inhibitor 2, a known inhibitor of PP1, was measured. As shown in FIG. 5, panel B, eIF-2($\alpha^{32}$P) phosphatase in the S10 fraction from wild-type virus- or R8300 virus-infected cells was similarly sensitive to Inhibitor 2 with a 50% reduction in the rate of dephosphorylation attained at approximately 90 and 120 µg of Inhibitor 2/ml, respectively. This suggests that activated eIF-2($\alpha^{32}$P) phosphatase is derived from PP1. However, the concentration of Inhibitor 2 required for inhibition of the activated eIF-2(µP) phosphatase appears to be much higher than that required to inhibit eIF-2($\alpha^{32}$P) phosphatase in mock-infected cells and also much higher than that required to inhibit PP1$\alpha$ in cell extracts. See Cohen, *Methods in Enzymology* 201:389–398 (1991). This could be due to the possible association of $_{\gamma_1}34.5$ with HeLa cell PP1$\alpha$, resulting in phosphatase activity directed specifically at eIF-2 ($\alpha$P), as suggested by the results shown in FIG. 4.

EXAMPLE 11

The Activated Phoshatase Activity is Specific for eIF-2$\alpha$

Figure 5D:
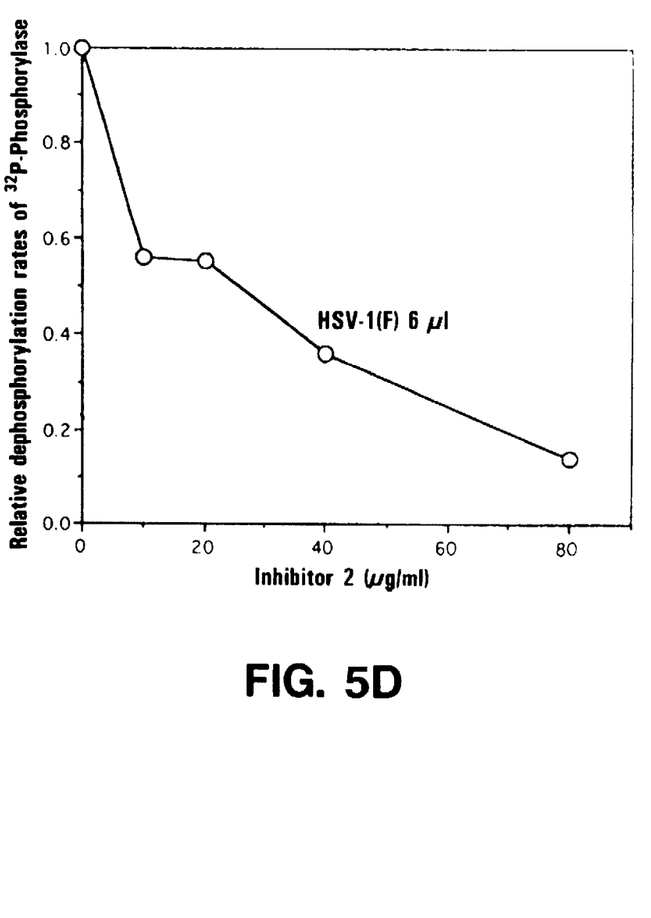
FIG. 5D shows the effect of inhibitor 2 on the relative rate of $^{32}$P-phosphorylase phosphatase activity.

By way of confirmation that eIF-2($\alpha^{32}$P) phosphatase is specifically activated in infected cells, the dephosphorylation of $|^{-32}$P$|$ phosphorylase, a known substrate of serine/threonine phosphatases, by lysates of HeLa cells mock infected or infected with wild type virus was examined. The results (FIG. 5C) showed that the $^{32}$P-phosphorylase phosphatase activity of HSV-1(F)-infected cells is only one half that of mock-infected cells. The activity responsible for the dephosphorylation of $^{32}$P-phorphorylase in wild type virus infected cells is sensitive to Inhibitor 2 (FIG. 5D). The observation that phorphorylase phosphatase activity in wild type virus-infected cells is significantly reduced relative to that of mock-infected cells suggests that the mechanism of activation of eIF-2($\alpha$P) phosphatase may involve association of the $_{\gamma_1}34.5$ gene product with a portion of the cellular PP1$\alpha$, converting this fraction to a phosphatase activity that is specific for eIF-2($\alpha$P).

EXAMPLE 12

Cell-Free Systems for Identification of Inducers and Inhibitors of Programmed Cell Death The observations described above that programmed cell death is associated with phosphorylation of eIF-2$\alpha$ and the shut-off of protein synthesis and that proteins such as $_{\gamma_1}34.5$ and GADD (MyD116) prevent the shutoff of protein synthesis by redirecting PP1$\alpha$ to dephosphorylate eIF-2$\alpha$ to enable continued protein synthesis despite the presence of activated PKR, were exploited to prepare cell-free systems for identifying candidate inducers or inhibitors of programmed cell death.

As is evident from the foregoing examples, cell-free systems for identifying inhibitors of programmed cell death according to the invention comprise phosphorylated eIF-2$\alpha$ and PP1$\alpha$. The eIF-2$\alpha$ may be phosphorylated with $^{32}$P. The system may further comprise a post-ribosomal supernatant of cells such as HeLa cells, SK-N-SH cells or other eucaryotic cells and/or a suitable buffer. A candidate inhibitor of programmed cell death is then introduced into the system and its effect on the level of eIF-2$\alpha$ phosphorylation is determined as described above. Inhibitors of programmed cell death are identified by their ability to decrease the level of phosphorylation of eIF-2$\alpha$ by, for example, redirecting PP1$\alpha$ to dephosphorylate eIF-2$\alpha$. Similarly, inhibitors of programmed cell death may be identified by their ability to prevent the phosphorylation of eIF-2$\alpha$. The ability of a candidate inhibitor of programmed cell death may also be identified by its ability to interact with PKR in a cell-free system.

Cell-free systems according to the invention are also useful for identifying inducers of programmed cell death. Thus, such systems comprise eIF-2$\alpha$, PP1$\alpha$ and a suitable phosphate donor such as ATP or an ATP analog. ATP may be $_{\gamma}{}^{32}$ATP. The cell-free system may additionally comprise a post-ribosomal supernatant derived from eukaryotic cells. The cell-free system may additionally comprise PKR. Such inducers are identified by their ability to phosphorylate or to maintain the level of phosphorylated eIF-2$\alpha$ by, for example, directing PP1$\alpha$ or PKR to phosphorylate eIF-2$\alpha$ in the presence of a suitable phosphate donor such as ATP or an ATP analog (which may be $_{\gamma}{}^{32}$P-labeled ATP) when introduced into the cell-free system.

The level of phosphorylation of eIF-2$\alpha$, and the phosphatase and phosphorylase activities associated with the phosphorylation and dephosphorylation of eIF-2$\alpha$ are measured are described, for example, in Examples 4, 5, and 9 above. The rate of the phosphatase and/or phosphorylase reaction may also be measured and the data analyzed using, for example, Michaelis-Menten analysis in order to more fully characterize and quantitate the respective dephosphorylation and phosphorylation reactions.

In accordance with the invention, varying concentrations of inhibitor or inducer are introduced in the cell-free systems of the invention in order to ascertain the optimal concentrations at which the substances exert their effects. Human PP1α and eIF-2α are preferred in the practice of the present invention. The use of recombinantly produced PP1α and eIF-2α are also within the scope of the invention. Analogs or homologs of eIF-2α and/or PP1α derived from other eukaryotes or prokaryotes are also within the scope of the invention as are eIF-2α and PP1α prepared by recombinant methods.

Phosphorylated (labeled) eIF-2α produced in the cell-free system of the invention may be separated from other components of the system by electrophoresis or by chromatographic methods. By way of example, labeled eIF-2α may be separated on denaturing polyacrylamide gels after which the separated components may be transferred to, for example, a nylon or nitrocellulose membrane followed by exposure to X-ray film. Relative levels of phosphorylation are then determined after developing the exposed X-ray film and quantifying the density of bands corresponding to eIF-2α by, for example, densitometry. The autoradiograph may also be used to localize the bands on the membrane corresponding to labelled eIF-2α after which they may be excised from the membrane and counted by liquid scintillation or other counting methods. eIF-2α and PP1α may be of mammalian origin.

The foregoing was presented by way of non-limiting example and it should not be construed to limit the present invention as set out in the appended claims. All references cited herein are hereby incorporated by reference in their entirety.

We claim:

1. A method for identifying inhibitors of programmed cell death in a cell-free system, the method comprising the steps of:

(a) preparing a cell-free system comprising phosphorylated eIF-2α and protein phosphatase 1α (PP1α);

(b) introducing into the cell-free system of step (a) a candidate inhibitor of programmed cell death and allowing the resulting mixture to incubate; and,   (c) measuring the level of phosphorylation of eIF-2α resulting from step (b);

wherein an inhibitor of programmed cell death decreases or prevents increase of the level of phosphorylation of eIF-2α that accompanies programmed cell death when compared to a control.

2. The method of claim 1 wherein the phosphorylated eIF-2α is [$^{32}$P]-labeled eIF-2α.

3. The method of claim 1 wherein the cell-free system comprises a post-ribosomal supernatant derived from eukaryotic cells.

4. The method of claim 3 wherein the phosphorylated eIF-2α is [$^{32}$P]-labeled eIF-2α.

5. The method of claim 3 wherein the post-ribosomal supernatant is derived from mammalian cells infected with a herpes simplex virus lacking expressible $_{\gamma_1}$34.5 genes.

6. The method of claim 3 wherein said eukaryotic cells are mammalian cells.

7. The method of claim 1 wherein the phosphorylated eIF-2α is prepared by reaction in a mixture comprising eIF-2α, hemin controlled translational repressor, and ATP or an analog thereof.

8. The method of claim 7 wherein the mixture further comprises a buffer.

9. The method of claim 1 wherein the cell-free system of step (a) further comprises a buffer.

10. A method for identifying inducers of programmed cell death in a cell-free system, the method comprising the steps of:

(a) preparing a cell-free system comprising eIF-2α, protein phosphatase 1α (PP1α), and ATP or an analog thereof;

(b) introducing into the cell-free system of step (a) a candidate inducer of programmed cell death and allowing the resulting mixture to incubate; and,   (c) measuring the level of phosphorylation of eIF-2α resulting from step (b);

wherein an inducer of programmed cell death increases or prevents decrease of the level of phosphorylation of eIF-2α that accompanies programmed cell death when compared to a control.

11. The method of claim 10 wherein the cell-free system further comprises double-strand RNA-dependent protein kinase (PKR).

12. The method of claim 10 wherein the ATP is $_\gamma$$^{32}$P-labeled ATP.

13. The method of claim 10 wherein the cell-free system further comprises a post-ribosomal supernatant derived from eukaryotic cells.

14. The method of claim 13 wherein the cell-free system further comprises double-strand RNA-dependent protein kinase (PKE).

15. The method of claim 13 wherein said eukaryotic cells are mammalian cells.

16. The method of claim 10 wherein the cell-free system of step (a) further comprises a buffer.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "primer"

( x i ) SEQUENCE DESCRIPTION: SEQ ID NO:1:

TGACTGGATG CAGAGGCGGC TCAGATTGTT C        31

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "primer"

( x i ) SEQUENCE DESCRIPTION: SEQ ID NO:2:

AGCGCGCAAT TAACCCTCAC TAAAG        25

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "primer"

( x i ) SEQUENCE DESCRIPTION: SEQ ID NO:3:

GCACTGAATT CTCCGACAGC GAGAAGCTCA AC        32

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "primer"

( x i ) SEQUENCE DESCRIPTION: SEQ ID NO:4:

GCACTGTCGA CATCTGGGGC ACAGGGTGGT GT      32